(12) United States Patent
Bartholomew et al.

(10) Patent No.: US 11,000,694 B2
(45) Date of Patent: May 11, 2021

(54) USE OF LASERS FOR TREATING AND REVERSING FIBROSIS

(71) Applicant: The Board of Trustees of the University of Illinois, Urbana, IL (US)

(72) Inventors: Amelia Bartholomew, Chicago, IL (US); Megan O'Connor, Chicago, IL (US); Rachana Patil, Chicago, IL (US)

(73) Assignee: THE BOARD OF TRUSTEES OF THE UNIVERSITY OF ILLINOIS, Urbana, IL (US)

( * ) Notice: Subject to any disclaimer, the term of this patent is extended or adjusted under 35 U.S.C. 154(b) by 392 days.

(21) Appl. No.: 14/923,101

(22) Filed: Oct. 26, 2015

(65) Prior Publication Data

US 2016/0114183 A1    Apr. 28, 2016

Related U.S. Application Data

(60) Provisional application No. 62/068,412, filed on Oct. 24, 2014.

(51) Int. Cl.
    *A61N 5/06*        (2006.01)
    *A61K 35/28*       (2015.01)
    *A61N 5/067*       (2006.01)

(52) U.S. Cl.
    CPC .......... *A61N 5/0613* (2013.01); *A61K 35/28* (2013.01); *A61N 2005/067* (2013.01); *A61N 2005/0663* (2013.01)

(58) Field of Classification Search
    CPC .......................... A61N 5/06–2005/073; A61B 2018/00315–2018/00565
    USPC ........ 604/20; 606/2–3, 9–13; 607/80, 88–89
    See application file for complete search history.

(56) References Cited

U.S. PATENT DOCUMENTS

| 4,930,504 A * | 6/1990 | Diamantopoulos .. A61N 5/0616 250/494.1 |
| 5,913,884 A | 6/1999 | Trauner et al. |
| 6,395,016 B1 | 5/2002 | Oron et al. |
| 6,413,267 B1 | 7/2002 | Dumoulin-White et al. |
| 6,746,473 B2 | 6/2004 | Shanks et al. |

(Continued)

FOREIGN PATENT DOCUMENTS

WO    2014035215 A1    3/2014

OTHER PUBLICATIONS

Aggarwal, S. and M. F. Pittenger (2005). "Human mesenchymal stem cells modulate allogeneic immune cell responses." Blood 105(4): 1815-1822.

*Primary Examiner* — Jonathan T Kuo
(74) *Attorney, Agent, or Firm* — Licata & Tyrrell P.C.

(57) ABSTRACT

A method for treating a subject having a diseased or atrophic state of fibrotic tissue, kidney disease and associated nerve endings, or for promoting tissue regeneration in muscle tissue is accomplished through exposing the tissue with a laser light having a wavelength of about 400 nm to about 700 nm, or more preferably having a wavelength of about 405 nm, about 532 nm, about 635 nm, or a combination thereof. Subsequent to exposure, mesenchymal stem cells can be administered to the subject. After the administration of mesenchymal stem cells, the tissue is further exposed to laser light having a wavelength of about 400 nm to about 700 nm, or a laser light having a single wavelength of about 400 nm to about 700 nm. The mesenchymal cells can be interferon gamma activated.

21 Claims, 10 Drawing Sheets

(56) References Cited

U.S. PATENT DOCUMENTS

| | | | |
|---|---|---|---|
| 7,540,869 B2* | 6/2009 | Altshuler | A61B 18/203 |
| | | | 128/898 |
| 7,551,653 B2 | 6/2009 | Spiekermann et al. | |
| 7,922,751 B2 | 4/2011 | Shanks et al. | |
| 9,011,840 B2 | 4/2015 | Bartholomew et al. | |
| 2004/0010298 A1* | 1/2004 | Altshuler | A61B 18/203 |
| | | | 607/88 |
| 2005/0261750 A1* | 11/2005 | McDaniel | A61B 18/203 |
| | | | 607/86 |
| 2007/0260297 A1* | 11/2007 | Chariff | A61N 5/0619 |
| | | | 607/89 |
| 2008/0269849 A1* | 10/2008 | Lewis | A61N 5/0613 |
| | | | 607/91 |
| 2009/0149844 A1* | 6/2009 | Altshuler | A61B 18/203 |
| | | | 606/9 |
| 2011/0044958 A1* | 2/2011 | Bartholomewq | C12N 5/0663 |
| | | | 424/93.7 |
| 2011/0060266 A1* | 3/2011 | Streeter | A61N 5/0613 |
| | | | 604/20 |
| 2012/0041521 A1 | 2/2012 | Oron et al. | |
| 2013/0317572 A1 | 11/2013 | Zhu et al. | |
| 2015/0141901 A1 | 5/2015 | Lichtbroun et al. | |

\* cited by examiner

USE OF LASERS FOR TREATING AND REVERSING FIBROSIS

CROSS REFERENCE TO RELATED PATENTS

This application claims the benefit of U.S. Provisional Patent Application No. 62/068,412 filed Oct. 24, 2014, which is incorporated by reference.

FIELD OF THE INVENTION

The present disclosure relates generally to methods of treating fibrosis. More specifically, the disclosure presents methods of using laser light of various wavelengths alone or in combination with mesenchymal stem cell therapy for treating and reversing conditions related to diseased or atrophic states of fibrotic tissue and promoting tissue regeneration.

BACKGROUND OF THE INVENTION

A. Renal Fibrosis and the Public Health Problem of Kidney Failure

Kidney disease, including both acute and chronic, is the 8$^{th}$ leading cause of death in the United States (US) with over 50,000 deaths in 2010 alone. Chronic Kidney Disease (CKD), affects 23 million adults in the US accounting for 11.5% of the population. Progression to chronic kidney disease is marked by fibrosis of both the tubular epithelium as well as the glomeruli with overexpression of extracellular matrix (ECM) proteins such as collagen. Fibrosis is the formation of excess fibrous connective tissue (such as collagen and glycosaminoglycan) in an organ or tissue, generally from a reparative or reactive process. Stimuli to initiate fibrosis include: sustained presence of pro-sclerotic cytokines, overcrowding of protein traversing the proximal tubule, and renal capillary vasoconstriction; all of which predominate in patients with diabetes and hypertension. The sequelae of persistent high blood pressure or high concentrations of blood sugar can induce an inflammatory state within the kidney, mobilizing macrophages, dendritic cells, and lymphocytes to infiltrate renal parenchyma and secrete pro-inflammatory cytokines such as tumor necrosis factor (TNF) and Transforming growth factor β (TGF-β$_1$). Baseline proliferative activity, though low, is rapidly replaced by progressive increase in apoptotic activity, particularly in the tubular endothelium. In the glomeruli, the reduced ability of endothelial proliferation contributes to the glomerular and peritubular capillary loss observed in fibrosis and glomerulosclerosis. Chronic inflammatory processes are followed by myofibroblast proliferation with a corresponding creation of a degenerative extracellular matrix environment associated with chronic kidney disease and loss of function. At present, no treatment exists for the reversal of renal fibrosis.

B. Effect of Lasers and Radiation on Tissue Regeneration

Low level laser therapy (LLLT) is currently being used to alter cellular activity in clinical applications including pain reduction, inflammatory relief, liposuction, and acne clearance by stimulating cellular proliferative activity. Laser-mediated improvement in wound healing is characterized by both enhanced tissue repair and inhibition of tissue degeneration. The overall mechanism by which low level light laser therapy affects cells is not well-characterized. One component of phenomenon is believed to be the transfer of energy to the cell which then can be used for various activities which otherwise may not occur with the rapidity or efficiency due to limits of cell energy. At the molecular level, such photobiomodulation is based on the ability of molecular chromophores and photo-acceptors to absorb the photons presented by the laser. Chromophore and photo-acceptor distribution may vary according to tissue type; therefore, tissue specific therapies are required to optimize energy delivery. Additionally, there are many molecules that are able to absorb the photons, including hemoglobin, melanin, and water, each molecule type prefers to engage a specific range of light color. Red, green, and violet wavelengths have been reported to promote proliferation of a variety of cells in vitro with results that demonstrate the cell specific preference to a certain wavelength. For example, red light was shown to promote proliferation in mouse skin fibroblasts, but chicken embryo fibroblast increased proliferation in response to green light. Cytochrome c oxidase of the mitochondrial respiratory chain can absorb nearly 50% of infrared light produced by a laser making this molecule the predominant target of laser therapy. Photon absorption can lead to electron transfer reactions, with subsequent increased production of ATP and nitric oxide (NO). Nitric Oxide (NO), serves to activate vasodilation, can operate as a neurotransmitter, and inhibits cell apoptosis through alterations on the enzymatic work of multiple caspases.

Efforts to use low level laser therapy in patients has seen some success, for example U.S. patent application Ser. No. 13/902,749 to Zhu et al. discloses a method of treating neuronal conditions in a patient. This method requires implantation of an optical element in the patient. LLLT has also been used to treat fibrosis, such as in the methods disclosed by U.S. Pat. No. 5,913,884 to Trauner et al. where laser irradiation is used to treat fibrotic tissue after administering a photosensitizing agent to the subject. This method relies on the photosensitizing agent, when photoactivated by laser light to produce a cytotoxic effect, to kill specific cell populations such as macrophages, thereby inhibiting fibrosis.

C. Mesenchymal Stem Cells and Tissue Regeneration Following Fibrosis

Bone marrow derived mesenchymal stem cells (MSC), multipotent adult stem cells, exhibit significant potential as therapeutic agents due to their ability to differentiate into a number of tissue types as well as their ability to reduce inflammation, promote regenerative signals amongst other cell types such as macrophages and endothelial cell, and enhance the orderly production of matrix. When MSCs encounter sites of inflammation, several cytokines and growth factors are produced including nerve growth factors as well as endothelium growth factors such as vascular endothelial growth factor VEGF which promotes endothelial and vascularity remodeling. MSCs also initiate the transition of pro-inflammatory M1 macrophages into suppressor M2 macrophages which work to restore matrix deposition into a healthy, organized microenvironment. Transforming growth factor β (TGF-β1), is an important cytokine in the initial immune response to injured tissue secreted by M2 macrophages; yet, when abnormally sustained in the microenvironment, pathological amounts of extracellular matrix is laid down leading to fibrosis demonstrating dysregulated TGF-β production as a prominent feature of kidney fibrosis. Interleukin 10 (IL-10), an anti-inflammatory cytokine produced by M2 macrophages, may reduce the fibrotic effects of TGF-β, preventing collagen synthesis and further fibrotic progression. MSCs tend to home towards acute inflammation, and are less able to migrate through fibrotic tissues, thereby, reducing their influence on regeneration in fibrosis. Facilitating the regenerative attributes of therapeutic MSCs may provide a new strategy to address and reverse tissue fibrosis.

By way of example, U.S. patent application Ser. No. 13/264,755 to Oron et al. discloses administering phototherapy to an injured subject by irradiation of bone marrow to stimulate mesenchymal stem cell migration to the site of tissue injury. This method does not involve direct irradiation of the damage tissue itself, but rather irradiation at a site removed from the place of injury. U.S. patent application Ser. No. 14/534,779 to Lichtbroun et al. further discloses the administration of a composition and the subsequent irradiation of various tissues with laser light which increase mesenchymal stem cell migration to a wound site.

Despite these advances in the use of low level laser therapy and mesenchymal stem cells to treat conditions such as fibrosis in a subject, each of the disclosed methods suffer from various drawbacks such as the use of photosensitizer or similar compounds, which may have some side effects, as well as the need to build up a certain level of photosensitizer in the target tissue for maximum effectiveness. In other methods, there is no direct irradiation of the damaged tissue itself, or require the implantation of a diode. Accordingly, there is a need for a low level laser light treatment of various diseases, including fibrosis, which does not rely on photosensitizers or other composition, and can allow for direct irradiation of the damages tissue. The present disclosure addresses these needs.

The present invention and its attributes and advantages will be further understood and appreciated with reference to the detailed description below of presently contemplated embodiments, taken in conjunction with the accompanying drawings.

SUMMARY OF THE INVENTION

The present disclosure provides for a method for treating diseased or fibrotic tissue such as pulmonary fibrosis, renal fibrosis, cardiac scaring, heart failure post myocardial infarction, liver cirrhosis, kidney nerve endings and dermal scaring to reduce the levels of fibrosis, as well as to promote regeneration of healthy tissue in the place of fibrotic tissue. Organ tissue such as heart tissue, kidney tissue or other muscle tissue may also be exposed to laser light to promote tissue regeneration. The method achieves this goal through the use of laser light irradiation of diseased tissue either alone, or in combination with the administration of stem cells. The exposure to laser light can be of a single wavelength, or of multiple wavelengths.

In one aspect, laser light of about 400 nm to about 700 nm is used to expose and treat conditions related to diseased or atrophic states of fibrotic tissue. Preferably, the laser light is selected from a wavelength of about 405 nm, about 532 nm, about 635 nm or combinations thereof. The fibrotic tissue can be exposed to sequential or simultaneous irradiation of different portions of the tissue by at least a single scan, or by two or more scans of the tissue. Subsequent to exposure, stem cells, preferably mesenchymal stem cells can be administered to the subject. The mesenchymal stem cells can be activated by interferon gamma. In some instances, the interferon gamma activated mesenchymal stem cells are MHC Class II+ cells. In further embodiments, a second exposure step is performed after the administration of the mesenchymal stem cells wherein the laser light of the second exposure step is of a wavelength of about 400 nm to about 700 nm.

In further aspects, the exposure of fibrotic tissue to laser light of a wavelength disclosed herein can reduce or slow cell death. This can be primarily accomplished through the reduction in apoptosis. Accordingly, fibrotic tissue can be exposed to laser light of a wavelength of about 400 nm to about 700 nm, and more preferably, exposed to a laser light of a wavelength of about 405 nm, about 532 nm, about 635 nm or combinations thereof. In other embodiments, mesenchymal stem cells may be administered to a subject, with or without further exposure to laser light of a wavelength disclosed herein subsequent to administration of the cells.

In another aspect, there is provided a method of treating kidney disease in a subject comprising exposing the kidney and/or associated nerves with laser light of about 400 nm to about 700 nm, and more preferably of laser light with a wavelength of about 405 nm, about 532 nm, about 635 nm or combinations thereof. The kidney can be sequentially or simultaneously irradiated over different portions of the kidney and associated nerves. Furthermore, mesenchymal stem cells can be administered to the subject after exposure of the kidney and/or associated nerves with laser light. The mesenchymal stem cells can be activated with interferon gamma, and in some embodiments, the interferon gamma activated mesenchymal stem cells can be MHC Class II+ cells.

In other aspects, the method of a treating kidney disease comprises first exposing the kidney and/or associated nerves two or more times to laser light of a wavelength of about 400 nm to about 700 nm, and preferably of laser light with a wavelength of about 405 nm, about 532 nm, about 635 nm or combinations thereof prior to administration of mesenchymal stem cells, followed by exposing the kidney again to laser light having a wavelength of about 400 nm to about 700 nm subsequent to administering the mesenchymal stem cells, and more preferably a wavelength of about 405 nm, about 532 nm or about 635 nm. In other embodiments, the second exposure is with a laser light having a single wavelength of about 400 nm to about 700 nm, and more preferably a single wavelength of about 405 nm, about 532 nm or about 635 nm.

In further embodiments, the method of treating kidney disease and/or associated nerves comprises exposing the kidney and/or associated nerves to laser light having a wavelength of about 405 nm, about 532 nm and about 635 nm, then administering mesenchymal stem cells to the kidney, and subsequently exposing the kidney to laser light having a wavelength of about 635 nm.

In still further embodiments, there is provided a method of promoting tissue regeneration in subject in need thereof by exposing a specific tissue to a laser light of about 400 nm to about 700 nm, and more preferably of laser light with a wavelength of about 405 nm, about 532 nm, about 635 nm or combinations thereof. The tissue can be sequentially or simultaneously irradiated over different portions of the tissue. Furthermore, mesenchymal stem cells can be administered to the subject after exposure of the tissue to laser light. The mesenchymal stem cells can be activated with interferon gamma, and in some embodiments, the interferon gamma activated mesenchymal stem cells can be MHC Class II+ cells. In other embodiments, at least a second exposure to laser light may be performed subsequent to administration of mesenchymal stem cells using any combination of laser light wavelengths as described herein, or with a laser light of a single wavelength. In some embodiments, the regenerated tissue is an internal organ such as, but not limited to, the kidney or heart. In other embodiments, the regenerated tissue includes muscle, connective, nervous, endothelial, and epithelial tissue.

In further embodiments, exposure to laser light increases or improves endothelial cell or epithelial cell proliferation and/or survival. In other embodiments, the exposure increases or improves organ epithelial cell proliferation and/or survival.

BRIEF DESCRIPTION OF THE DRAWINGS

The preferred embodiments of the invention will be described in conjunction with the appended drawings provided to illustrate and not to the limit the invention, where like designations denote like elements, and in which.

DETAILED DESCRIPTION OF EMBODIMENTS OF THE INVENTION

Figure 1:
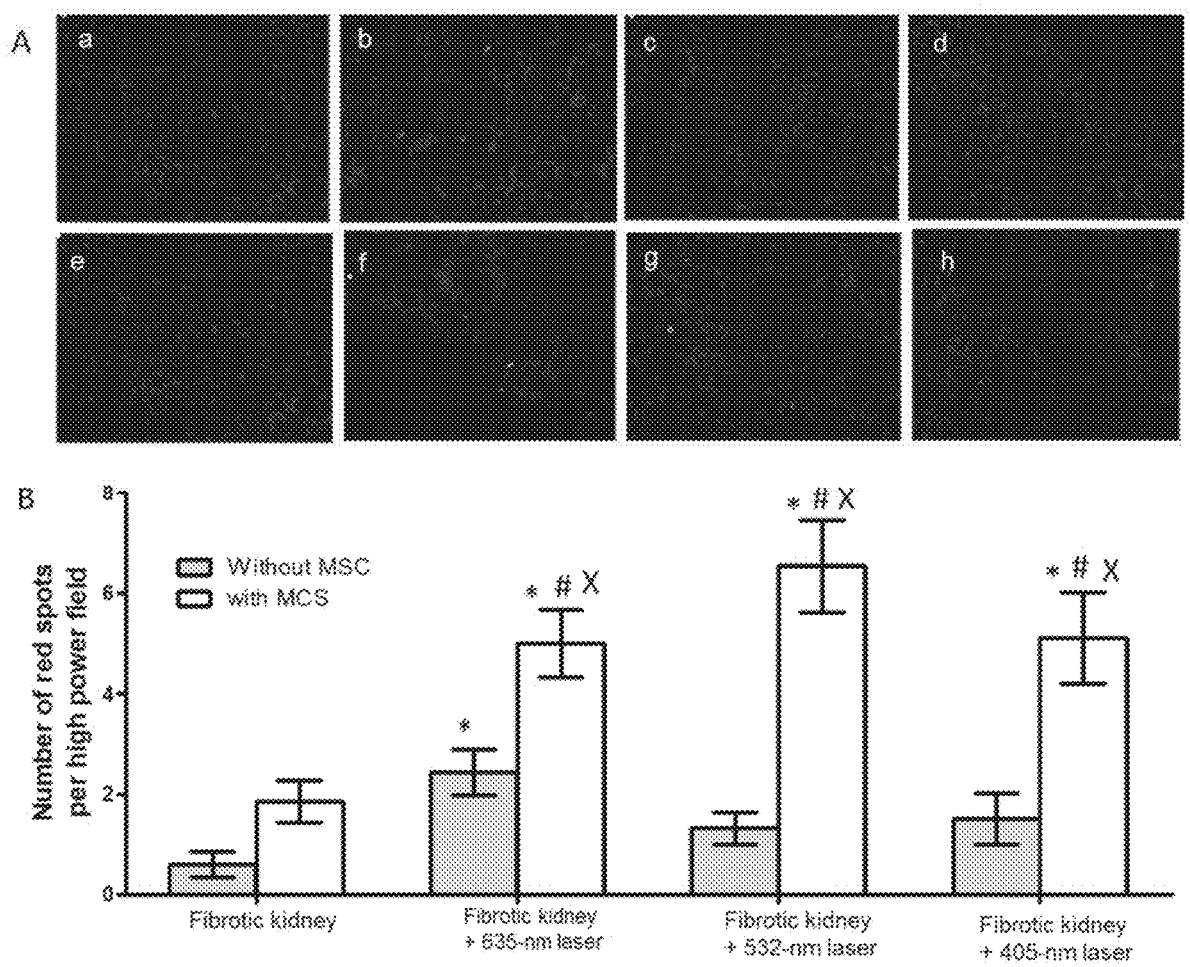
FIG. 1 illustrates mitochondrial activity in fibrotic kidney stained with Mitotracker Red CMXRos. A), Images acquired by microscopy with 20× subject lens. (a) Fibrotic kidney, (b) fibrotic kidney+635-nm laser, (c) fibrotic kidney+532-nm laser, and (d) fibrotic kidney+405-nm laser, (e) fibrotic kidney with MSC, (f) Fibrotic kidney+635-nm laser with MSC, (g) fibrotic kidney with 532-nm laser with MSC, (h) fibrotic kidney with 405-nm laser with MSC. Spots in the image are the accumulations of fluorescent dye in mitochondria. B), The accumulated fluorescent dye was counted by microscopy with 20× objective lane, expressed as mean per high power field (20×). *; p-value<0.05 vs fibrotic kidney without MSC, #, p-value<0.05 vs fibrotic kidney with MSC. $^X$; p-value<0.05 vs corresponding laser treated fibrotic kidney.

The present disclosure provides for a method of using laser light alone or in conjunction with mesenchymal stem cell treatment to treat diseased or atrophic states of fibrotic tissue which require initiation of and perpetuation of the regenerative response. Because of both the proliferative potentiation, pro-angiogenic, and anti-apoptotic effects of this therapy, conditions in which damaged vasculature and parenchymal tissue undergoing apoptosis, such as lethal total body irradiation (range 2Gy-10Gy) may also benefit. In conditions of muscle rehabilitation status post trauma or stroke in which the muscle has diminished regenerative potential and/or scarring, this therapeutic approach, because of its beneficial effects of retaining mesenchymal stem cells at the injury site for site specific differentiation, reduction of apoptosis following muscle training for more efficient hypertrophy, and promotion of angiogenesis for more efficient muscle hypertrophy or new growth, could also be applied for enhanced strength or enhanced fill of tissue defects.

As used herein the following abbreviations shall have the following meanings: BrdU for 5-bromo-2'-deoxyuridine; CKD for Chronic Kidney Disease; ECM for Extracellular Matrix; HE for Hematoxylin and Eosin; IL for Interleukin; LLLT for Low Level Laser Therapy; MSC for Mesenchymal Stem Cells; NO for Nitric Oxide; TGF for Transforming Growth Factor; TNF for Tumor Necrosis Factor; and UUO for Unilateral Ureter Obstruction.

As used herein, the term "about" refers to an approximately +/−10% variation from a given value. It is to be understood that such a variation is always included in any given value provided herein, whether or not it is specifically referred to.

A "patient," "subject," or "host" to be treated by the subject method may mean either a human or non-human animal, such as a mammal, a fish, a bird, a reptile, or an amphibian. Thus, the subject of the herein disclosed methods can be a human, non-human primate, horse, pig, rabbit, dog, sheep, goat, cow, cat, guinea pig or rodent. The term does not denote a particular age or sex. Thus, adult and newborn subjects, as well as fetuses, whether male or female, are intended to be covered. In one aspect, the subject is a mammal.

"Treating" a mammal having a disease or disorder means accomplishing one or more of the following: (a) reducing the severity of the disease; (b) arresting the development of the disease or disorder; (c) inhibiting worsening of the disease or disorder; (d) limiting or preventing recurrence of the disease or disorder in patients that have previously had the disease or disorder; (e) causing regression of the disease or disorder; (f) improving or eliminating the symptoms of the disease or disorder; and (g) improving survival.

As used herein "exposure" means treating with a laser for a time useful to the invention. In one embodiment, exposure means to treat with a laser applied in a pulse, wherein the pulse is applied for a particular duration. The range of pulse durations are in the hundreds of picoseconds to hundreds of nanoseconds (for example, about 100, 200. 300, 400, 500. 600, 700, 800, 900 picoseconds, or about 1, 2, 3, 4, 5, 6, 7, 8, 9, 10, 12, 15, 20, 25, 30, 35. 40, 45, 50, 75, 100. or 200 nanoseconds). It is understood that the actual pulse length will vary somewhat based on the limitations of the laser and the switching rate/shutter speed. The laser may also be applied in a continuous irradiation mode.

In another embodiment, "exposure" means to treat with a laser of a particular pulse repetition (pulse frequency). Optimal pulse frequencies range from about 1 Hz to about 100 kHz (for example, 0.001, 0.01, 1, 10, 100 kHz), with typical pulse frequencies in the 1, 2, 3. 4, 5, 6, 7, 8, 9, 10, 20, 30, 40, 50 or 100 kHz frequency. It is understood that the actual pulse frequency will vary somewhat based on the limitations of the laser and the switching rate/shutter speed. In another embodiment, "exposure" means to treat with a laser of a particular wavelength where the range of wavelengths can range from the visible light portion of the electromagnetic spectrum (approximately 350 nm to 700 nm, for example, 300, 350, 375, 400, 425, 450, 475, 500, 525, 550, 575, 600, 625, 650, 675, 700). In another embodiment, "exposing" means to expose a subject to a laser with a particular peak energy, where the range of pulse energy is 1 microjoule to ($1\times10^{-6}$ J) to 1 Joule (for example, 1, 10, 20, 30 40, 50, 100, 200, 300, 400, 500 microjoules. 1, 2, 3, 4, 5, 10, 20. 30, 40, 50, 100, 200, 300, 400 500 millijoules, or 0.6, 0.7. 0.8, 0.9. and 1.0 Joule).

In another embodiment, "exposure" means to treat with a laser of a particular power density or irradiance, where the range of irradiance is 0.1 to 10 $W/cm^2$ (for example, about 0.1, 0.2, 0.3, 0.4, 0.5, 0.6, 0.7, 0.8, 0.9, 1, 2, 3, 4, 5. 6, 7, 8, 9, or 10 W/cm) and are typically about 1-4 W/cm.

In another embodiment, "exposure" means to treat with a laser for a particular length of time. The range of exposure times can be about 10 seconds to about 600 seconds (for example, about 10, 20, 30, 40, 50, 60, 70, 80, 90, 100, 150, 200, 250, 300, 350, 400, 450, 500, 550, 600 seconds).

In another embodiment, "exposure" means to treat with a laser a particular area of the subject. Typical treatment areas are about 1-300 mm in diameter (for example, 1, 2, 3, 4, 5, 6, 7, 8, 9, 10, 20, 30, 40, 50, 60, 70, 80, 90, 100 $mm^2$ etc. . . . ). Treatment may involve exposure of multiple areas of the subject.

As used herein, a "laser" refers to an electronic-optical device that emits coherent light radiation. A typical laser emits light in a narrow, low-divergence monochromatic (single-colored, if the laser is operating in the visible spectrum), beam with a well-defined wavelength. In this respect, laser light is in sharp contrast with such light sources as the incandescent light bulb, which emits light over a wide area and over a wide spectrum of wavelengths. The term "laser" further includes any laser that is currently available or may become available that can provide the appropriate pulse duration, power, and pulse frequency required by the methods of the instant invention. Currently available lasers that can be used in the methods of the invention include, but are not limited to gas vapor lasers, metal vapor lasers, pulse dye lasers, solid state lasers, semiconductor lasers and fiber lasers.

The method as disclosed herein may be used to treat conditions that are related to a diseased or atrophic state of fibrotic tissue to promote tissue regeneration through exposure of a subject with a laser light having a wavelength between 400 nm to 700 nm. Such diseased or atrophic state can include, for example, Pulmonary fibrosis, Cystic fibrosis, Cardiac scaring, Idiopathic pulmonary fibrosis, Cirrhosis of the liver, Atrial Fibrosis, Endomyocardial fibrosis, Myocardial infarction, heart status post myocardial infarction, Arthrofibrosis, Crohn's Disease, Dupuytren's contracture, Keloid or other dermal scarring, Mediastinal fibrosis, Myelofibrosis, Peyronie'disease, Nephrogenic systemic fibrosis, Progressive massive fibrosis, Retroperitoneal fibrosis, Scleroderma/systemic sclerosis, adhesive capsulitis or other conditions that involve fibrosis.

In some embodiments, the disease state is fibrosis of an internal organ, such as the kidney or heart. In some embodiments, the kidney is in a state of renal fibrosis. In still further embodiments, the diseased state is fibrosis of muscle tissue. The method may also treat nerves or nerve endings associated with the organ or muscle, such as, for example, kidney nerve endings.

In other embodiments, the method is used to promote tissue regeneration. Such tissues can include internal organs, components of the vasculature system (veins, arteries, capillaries etc.) and muscle tissue (smooth, skeletal and cardiac muscles). Internal organs can include, but are not limited, to the heart, liver, bile duct, kidney, stomach, spleen, lungs, brain, pancreas, gall bladder, colon, bladder and small intestine. Such a method may be particularly useful in subjects who have suffered a traumatic injury to an organ such a myocardial infarction or ischemia, as well as other injuries or conditions that lead to a deterioration and/or cell death in an organ. Other tissue types that may benefit from the methods disclosed herein include connective tissue, nervous tissue and epithelial tissue.

Connective tissue generally supports and holds together various organs or tissue structures of the body and can be composed of an extracellular matrix of proteins and glycoproteins. Connective tissue can include collagen and other elastic fibers, tendons, ligaments, dermal layers, adipose tissue, cartilage, bone, blood or lymph tissue.

Nervous tissue generally comprises neuron and their supporting cells. Such tissue includes nerves, spinal cord and the brain.

Epithelial tissue generally covers of all body surfaces, lines body cavities and hollow organs, and are the major tissue in various glands of the body.

Epithelial tissue performs a variety of functions that include protection, secretion, absorption, excretion, filtration, diffusion, and sensory reception. In some embodiments, the laser light exposure can improve or increase epithelial cell proliferation and/or survival including, but not limited to, cells lining the stomach, intestines, liver, pancreas, gall bladder, bladder, kidneys, heart, esophagus and lungs. This also includes epithelial cells forming, forming, for example, part of or lining ducts, glands, skin, capillary beds, nose, ears, eyes and reproductive organs.

In some embodiments, a laser light exposure can improve or increase organ epithelium cells proliferation and/or survival. The organ epithelium cells can be of any organ described herein.

In other embodiments, the laser light exposure can improve or increase endothelial cell proliferation and/or survival. Endothelial cells generally are found lining the interior of blood and lymphatic vessels.

In further embodiments, the exposure of fibrotic organs, or other tissue in need of regeneration can reduce or slow cell death in said organ or tissue. In some embodiments, the cell death that is reduced or slowed is apoptosis.

Apoptosis, also known as "programmed" cell death, classically involves the genetically determined elimination of cells and occurs normally during development and aging, and as a homeostatic mechanism to maintain cell populations in tissues. Apoptosis also occurs as a defense mechanism such as in immune reactions or when cells are damaged by, trauma, disease or toxic agents. Although there are a wide variety of stimuli and conditions, both physiological and pathological, that can trigger apoptosis, not all cells will necessarily die in response to the same stimulus. For example, Irradiation or drugs used for cancer chemotherapy results in DNA damage in some cells, which can lead to apoptotic death through a p53-dependent pathway.

Some cells express Fas or TNF receptors that can lead to apoptosis via ligand binding and protein cross-linking. As an example, some hormones, such as corticosteroids, may lead to apoptotic death in some cells although other cells are unaffected or even stimulated. Other cells have a default death pathway that must be blocked by a survival factor such as a hormone or growth factor. Whichever the case may be, it is clear that apoptosis is a coordinated and often energy-dependent process that involves the activation of a group of cysteine proteases called "caspases" and a complex cascade of events that link the initiating stimuli to the final demise of the cell. According to an aspect of the method, exposure is performed by delivering visible or infrared light energy to the desired tissues and/or associated nerves by positioning a probe including a source of coherent light on a body surface of the subject, and transcutaneously directing the energy from the probe toward the tissues and/or associated nerves. The source of coherent light may be a laser or a light-emitting diode.

According to another aspect of the method, exposure is performed by delivering visible or infrared light energy to the target tissues and/or associated nerves by positioning a laser probe beneath a body surface of the subject, and directing the energy from the probe toward the tissues and/or associated nerves.

It has been shown that low level laser therapy can be effective throughout the visible, near infrared and near ultraviolet regions. Laser diodes are currently available to cover only a limited part of the available spectrum, so other laser energy sources may be used. To obtain maximum benefit it may be desirable to stimulate the subject at two or more different wavelengths. The laser can be of a single wavelength laser or a multi-wavelength laser. Persons skilled in the art will be aware that various laser energy sources are known in the art for use in low-level laser therapy. Suitable lasers include Helium-Neon, Xenon-Chloride, Xenon-Fluoride, Helium-Cadmium, Rhodamine, Copper Vapor, Argon, Frequency Doubled Nd:YAG, Krypton, and Ruby lasers and also semiconductor diode lasers, examples of which are disclosed in U.S. patent application Ser. No. 10/583,444 and U.S. Pat. Nos. 6,413,267 and 6,395,016. Additionally, it may be advantageous to utilize at least one laser beam in the visible energy spectrum so that the operator can see the laser light as it impinges the subject's body and the area treated can be easily defined. Diodes of various other wattages may also be employed to achieve the desired laser energy for the given regimen.

The laser light can be delivered to the subject either directly or via optical transmission fiber.

The color of light emitted by a laser is determined by the wavelength traveled by its photons: a shorter wavelength corresponds with higher energy deliverance. Visible (350 nm to 750 nm wavelength) and infrared light (750 nm to 1400 nm wavelength) have both been reported to accelerate and facilitate wound healing, with better results from the visible light spectrum. Currently, red visible light (635 nm) is FDA approved for clinical application, but the in vivo extent of green (532 nm) and violet (405 nm) has not been fully examined.

In certain embodiments, the lasers are selected from low level light lasers of wavelengths of about 400 nm to 700 nm. In other embodiments, the laser wavelength is about 405 nm, about 532 nm, and about 635 nm and combinations thereof.

In other embodiments, the laser light has a wavelength of about 532 nm, and about 635 nm and combinations thereof.

In some embodiments, the laser light has a wavelength of about 405 nm. In other embodiments, the laser light has a wavelength of about 532 nm. In still further embodiments, the laser light has a wavelength of about 635 nm.

In other embodiments, the laser light can be combination of three laser light wavelengths (e.g. 405 nm, 532 nm and 635 nm for example) where the exposure is accomplished sequentially with individual laser lights of different wavelengths, or by two or more laser light wavelengths applied simultaneously.

In some situations, the methods disclosed herein provide for sequential or simultaneous exposure of different portions of a tissue (e.g. kidney, heart, muscle, nerve endings or any other tissue disclosed herein). The exposure may be a single pass of the laser light over the desired portion of tissue. In some embodiments, it may be desirable to perform multiple scans over the tissue. For instance, the user may make 2, 3, 4, 5, 6, 7, 8, 9, 10, 15, 20, 25, 30, 35, 40, 45, 50, 60, 70, 80, 90, 100, 150, 200 or more scans over the tissue. Each scan may be of the same or different laser light wavelength, and may be the same or different in duration, pulse length, energy, laser mode (continuous or pulsed) and length of time between scans.

In certain embodiments, the laser light is a continuous beam. In other embodiments, the laser light may be pulsed. Pulse duration controllers are connected to the laser energy sources to form a control circuit that controls the duration of each pulse of laser light emitted, referred to herein as the pulse width. Pulse widths from 0 to 100,000 Hz may be employed to achieve the desired treatment effect without adversely affecting the patient's tissue. The treatment goal is to deliver laser energy to the fibrotic tissues and associated nervous tissue Applying low level laser energy as described herein causes no immediate detectable temperature rise of the treated tissue. Low level laser energy penetrates the skin and is specific to the depth of the desired treatment. Consequently, the treated and surrounding tissue is not heated and is not damaged. Preferably the laser light is visible to the human eye so that the area of application is easily determined.

The laser device can optionally include optics for shaping the beam to create desired spot shapes, as described in U.S. Pat. No. 6,746,473. In an embodiment, laser energy is applied with a laser device capable of creating a linear spot shape. By using a line of laser light, the number of times the laser light must be scanned back and forth across the targeted area is minimized relative to a stationary single spot emission of light. The laser device may include an optical arrangement having a collimating lens and a line generating prism disposed in serial relation to the laser energy source and power source. The collimating lens and line generating prism receive and transform the generated beam of laser light into a line of laser light. As an alternative, a suitable electrical or mechanical arrangement or combination thereof could be substituted for or combined with the optical arrangement to achieve a desired spot shape.

Each laser beam exits the corresponding laser energy source and is shone through optical arrangements that produce beam spots of certain shapes. The beam spot is the cross-sectional shape and size of the emitted beam as it impinges the target area. For example, a laser beam of circular cross-section creates a circular beam spot as the laser light impinges the treatment area. If the laser beam is in the visible range, a circular beam spot can be seen on the treatment area of substantially the same diameter as the laser beam emitted from the laser energy source, provided the optical arrangement does not manipulate the laser beam. The laser beam can be manipulated, such as by collimation, refraction, masking, or another method of reshaping a laser beam, in order to produce beam spots of different sizes and shapes. In an embodiment, the laser beams are shaped to produce linear beam spots on the patient.

Each laser energy source can also be a laser scanning device such as the inventions described in U.S. Published Patent Application 2006/0095099. By using laser scanning devices, the line generating prism can be operated to scan laser light in any pattern. Parameters may be entered to program the laser energy sources in a required manner to achieve any desired laser treatment path upon the patient. The device may be programmed to direct the laser output into some regions more than others so that one region may have greater treatment than another region. The scan areas of optical arrangements from multiple laser energy sources may overlap, whether they emanate from the same housing or separate housings.

In some embodiments, the area of exposure to laser light is about 1 $cm^2$-400 $cm^2$, about 50 $cm^2$-350 $cm^2$, about 100 $cm^2$-300 $cm^2$, or about 150 $cm^2$-250 $cm^2$. In other embodiments, the area of exposure is about 300 $cm^2$.

In other embodiments, the energy density of the emitted laser light is about 1-5 $J/cm^2$, about 2-5 $J/cm^2$, about 3-5 $J/cm^2$ or about 4-5 $J/cm^2$. In some embodiments, the energy density of emitted laser light is about 2.9 $J/cm^2$.

In further embodiments, the length of exposure is preferably about 1-400 seconds, or more preferably, about 100-300 seconds, and most preferably about 300 seconds. Preferably, the exposure is of continuous irradiation.

In some embodiments, the laser treatment is used in combination with other types of treatments such as, but not limited to therapeutic molecules, immunosuppressant agents, proliferative agents and the like, and seeding the site of treatment with various cell types such as pluripotent stem cells.

A stem cell is commonly defined as a cell that is capable of renewing itself; and can give rise to more than one type of cell through asymmetric cell division. Stem cells typically give rise to a type of multipotent cell called a progenitor cell; progenitor cells, in turn, proliferate and differentiate into cells that populate the body.

Stem cells exist in many different tissues and many different types of mammalian stem cells have been characterized and cultured under favorable conditions to allow differentiation. Both adult and embryonic stem cells are able to differentiate into a variety of cell types and, accordingly, may be a source of replacement cells and tissues for tissues that are damaged in the course of disease or infection. For instance, stem cells can, after differentiation, carry out the unique functions of particular tissues, such as heart, liver, or neuronal tissue.

Stem cells can be embryonic stem cells, adult stem cells (also known as tissue specific stem cells) or induced pluripotent stem cells. Any type of stem cell may be used depending on various conditions, as well as a combination of types of stem cells. Some embodiments as disclosed herein use adult stem cells. In other embodiments, the adult stem cells are Mesenchymal stem cells.

Mesenchymal stem cells (MSCs) are non-hematopoietic cells that are capable of differentiating into specific types of mesenchymal or connective tissues including adipose, osseous, cartilaginous, elastic, neuronal, hepatic, pancreatic, muscular, and fibrous connective tissues. The specific differentiation pathway which these cells enter depends upon various influences from mechanical influences and/or endogenous bioactive factors, such as growth factors, cytokines, and/or local microenvironment conditions established by host tissues.

MSCs reside in a diverse host of tissues throughout the adult organism and possess the ability to 'regenerate' cell types specific for these tissues. Examples of these tissues include adipose tissue, umbilical cord blood, periosteum, synovial membrane, muscle, dermis, pericytes, blood, bone marrow and trabecular bone. MSC's may be isolated from any of these sources. MSCs may be derived from these sources individually, or the sources may be combined to produce a mixed population of MSCs from different tissue sources. Accordingly, one skilled in the art will understand that mesenchymal stem cells for use with the present invention may be selected upon individual patient characteristics and the end result sought. For example, if autologous mesenchymal stem cells are available in the form of adipocyte-derived cells, it will be useful to utilize this source instead of allogeneic cord-blood derived cells. Alternatively, cord blood derived mesenchymal stem cells may be more advantageous for use in situations where autologous cells are not available, and expansion is sought. In other situations, MSC's derived from bone morrow are used.

MSCs can be expanded ex vivo prior to use in an embodiment of the present application. For example, MSCs can be derived from the bone marrow of a subject and then maintained in culture. In other embodiments, MSCs can be isolated, preferably from bone marrow or adipose tissue, purified, and expanded in culture, i.e. in vitro, to obtain sufficient numbers of cells for use in the methods described herein. For example, human bone marrow preparations may be derived from the iliac crest of a subject. Nucleated cells can be isolated from the bone marrow preparations and plated in a suitable growth media. The cells are then passaged and maintained in culture media such as described, for example in patent application PCT/KR2013/007891 to Yang et al.

Accordingly, stem cells, and more preferably mesenchymal stem cells can be used to treat a diseased or atrophic states of fibrotic tissue, and in muscle regeneration as mentioned previously in conjunction with laser light irradiation of the diseased tissue.

In some embodiments, a subject with a diseased tissue of interest can be exposed to laser light with a wavelength as disclosed herein, and then administered stem cell treatment, preferably with MSC's. The stem cells can be delivered through conventional means such as, but not limited to surgical transplantation, needle injection and intravenous infusion.

In preferred embodiments, the fibrotic tissue (kidney, heart tissue, muscle tissue or nerve endings associated with each), kidneys or tissue in need of regeneration is exposed to laser light of a wavelength of about 400 nm to 700 nm, and more preferably of a laser wavelength selected from the group consisting of about 405 nm, about 532 nm, about 635 nm or a combination thereof. The subject is then administered an effective amount of MSC cells. As mentioned previously, the initial exposure to laser light can be a single scan, or multiple scans In further embodiments, after an initial scan(s) of laser light and the administration of MSC cells, the subject may be further irradiated with at least a second round of laser light. In other embodiments, the method disclosed herein comprises at least a second exposure to laser light having a wavelength of about 400 nm to about 700 nm, and more preferably of a laser wavelength selected from the group consisting of about 405 nm, about 532 nm, about 635 nm or any combination thereof. In other embodiments, the second exposure (or more) can be of a single laser light wavelength of about 400 nm to about 700 nm wherein the single laser light wavelength is preferably about 405 nm, 532 nm or about 635 nm. In some embodiments, the second or more exposure can be of at least two, or at least three wavelengths applied sequentially, or of just a single wavelength. In still further embodiments, prior to administration of MSC's, the tissue can be exposed one or more times to laser light of a wavelength disclosed herein, either in a single wavelength, of in any combination of laser light of a wavelength disclosed herein.

In further embodiments, MSC's can be administered multiple times and over a period of time, such as days or weeks. After an initial pre-administration exposure, the subject can be exposed to laser light of wavelength described herein, either as a single wavelength or as a combination of wavelengths. In some embodiments, MSC's are administered to a subject once a week over a period of two weeks. The subject is exposed to laser light at least three times per week with laser light of 405 nm, 532 nm and 635 nm, and then with an additional exposure to laser light of a wavelength of a single wavelength at least three times per week. Preferably, the additional exposure to laser light of a single wavelength is 635 nm.

In situations where a decrease in immunogenicity is sought, cells may be administered using immune suppressive agents. Said agents include soluble factors, membrane-bound factors, and enzymes capable of causing localized immune suppression. Examples of soluble immune suppressive factors include: IL-4, IL-10, IL-13, TGF-β, soluble TNF-receptor, and IL-1 receptor agonist. Membrane-bound immunoinhibitor molecules that may be transfected into or added to stem cells for use in practicing the current invention include: HLA-G, FasL, PD-IL, Decay Accelerating Factor, and membrane-associated TGF-β. Enzymes which may be administered in order to cause localized immune suppression include indolamine 2, 3 dioxygenase and arginase type II.

In some embodiments, the administered MSC's are activated with interferon gamma. In further embodiments, the administered interferon gamma activated MSC's are Major Histocompatibility (MHC) Class II+ cells.

Interferon gamma is a major pro-inflammatory cytokine secreted by activated T cells and Natural Killer cells. IFN-γ activated MSC's can influence T cell responses by modulating MSC inhibitory factors. These factors include, but are not limited to downregulating T cell activation, enhancing T cell negative signaling, altering T cells from a pro-inflammatory to an anti-inflammatory phenotype and interacting with antigen-presenting cells. Accordingly, Interferon gamma, or any other immunosuppressant or growth factor listed herein may be used to pre-activate the MSC's. In other embodiments, such factors may be co-administered with the MSC's, or, when needed, these factors can be used to supplement the pre-activated MSC's (as described, for example, in U.S. patent application Ser. Nos. 12/922,417 and 13/483,910).

Furthermore, various growth factors may be co-administered with the stem cells, or used to pre-activate the stem cells in order to extent viability/therapeutic activity of the cells. In detail, non-limiting examples of these factors include human growth hormone, growth hormone releasing hormone, growth hormone releasing peptide, interferons and interferon receptors (e.g., interferon-α, -β and -γ, water-soluble type I interferon receptor, etc.), granulocyte colony stimulating factor (G-CSF), granulocyte-macrophage colony stimulating factor (GM-CSF), glucagon-like peptides (e.g., GLP-1, etc.), G-protein-coupled receptor, interleukins (e.g., interleukin-1, -2, -3, -4, -5, -6, -7, -8, -9, -10, -11, -12, -13, -14, -15, -16, -17, -18, -19, -20, -21, -22, -23, -24, -25, -26, -27, -28, -29, -30, etc.) and interleukin receptors (e.g., IL-1 receptor, IL-4 receptor, etc.), enzymes (e.g., glucocerebrosidase, iduronate-2-sulfatase, alpha-galactosidase-A, agalsidase alpha and beta, alpha-L-iduronidase, butyrylcholinesterase, chitinase, glutamate decarboxylase, imiglucerase, lipase, uricase, platelet-activating factor acetylhydrolase, neutral endopeptidase, myeloperoxidase, etc.), interleukin and cytokine binding proteins (e.g., IL-18 bp, TNF-binding protein, etc.), macrophage activating factor, macrophage peptide, B cell factor, T cell factor, protein A, allergy inhibitor, cell necrosis glycoproteins, immunotoxin, lymphotoxin, tumor necrosis factor, tumor suppressors, metastasis growth factor, alpha-1 antitrypsin, albumin, alpha-lactalbumin, apolipoprotein-E, erythropoietin, highly glycosylated erythropoietin, angiopoietins, hemoglobin, thrombin, thrombin receptor activating peptide, thrombomodulin, factor VII, factor VIIa, factor VIII, factor IX, factor XIII, plasminogen activating factor, fibrin-binding peptide, urokinase, streptokinase, hirudin, protein C, C-reactive protein, renin inhibitor, collagenase inhibitor, superoxide dismutase, leptin, platelet-derived growth factor, epithelial growth factor, epidermal growth factor, angiostatin, angiotensin, bone growth factor, bone stimulating protein, calcitonin, insulin, atriopeptin, cartilage inducing factor, elcatonin, connective tissue activating factor, tissue factor pathway inhibitor, follicle stimulating hormone, luteinizing hormone, luteinizing hormone releasing hormone, nerve growth factors (e.g., nerve growth factor, cilliary neurotrophic factor, axogenesis factor-1, brain-natriuretic peptide, glial derived neurotrophic factor, netrin, neurophil inhibitor factor, neurotrophic factor, neuturin, etc.), parathyroid hormone, relaxin, secretin, somatomedin, insulin-like growth factor, adrenocortical hormone, glucagon, cholecystokinin, pancreatic polypeptide, gastrin releasing peptide, corticotropin releasing factor, thyroid stimulating hormone, autotaxin, lactoferrin, myostatin, receptors (e.g., TNFR(P75), TNFR (P55), IL-1 receptor, VEGF receptor, B cell activating factor receptor, etc.), receptor antagonists (e.g., IL-1-Ra etc.), cell surface antigens (e.g., CD 2, 3, 4, 5, 7, 11a, 11 b, 18, 19, 20, 23, 25, 33, 38, 40, 45, 69, etc.), monoclonal antibodies, polyclonal antibodies, antibody fragments (e.g., scFv, Fab, Fab', F(ab')2 and Fd), and virus derived vaccine antigens, keratinocyte growth factor (KGF), tumor necrosis factor (TNF), fibroblast growth factor (FGF) and interleukin-1 (IL-1), Keratinocyte Growth Factor-2 (KGF-2), platelet-derived angiogenesis factor (PDAF), vascular endothelial growth factor (VEGF), platelet-derived epidermal growth factor (PDEGF) and combinations thereof. Care must be taken when selecting growth factors to be used in combination with cells for the practice of the current disclosure, in order to avoid stimulation of fibrotic responses by use of said growth factors. One of skilled in the art may, without extensive experimentation, utilize various in vitro assays to screen for optimized combinations of growth factors with cells administered.

The following Examples are intended to illustrate the above invention and should not be construed as to narrow its scope. One skilled in the art will readily recognize that the Examples suggest many other ways in which the invention could be practiced. It should be understood that numerous variations and modifications might be made while remaining within the scope of the invention.

Example 1. Laser Synergy with Mesenchymal Stem Cells

Here, Applicants address the question whether a single treatment of one of three visible light wavelengths, 635 nm, 532 nm, and 405 nm (constant wave), affects hallmarks of ongoing renal fibrosis in a mouse unilateral ureteral obstruction model. To this aim, Applicants investigated the frequency of mitochondrial activation, apoptosis, cellular proliferation with a specific focus on endothelial cells, and TGF-beta tissue content. In addition, Applicants investigated the possibility of synergistic effects between laser wavelength and mesenchymal stem cells. The data showed laser treatments synergized with MSC to improve the beneficial effects of MSC; each wavelength contributed to either mitigation of activities associated with fibrosis or the pro-regenerative activities of mitochondrial activation and endothelial proliferation.

Materials and Methods

Animals

Male C57BL/6 mice, 12 weeks old, underwent right unilateral ureter obstruction (UUO) to induce renal parenchymal fibrosis. Following ketamine/xylazine anesthesia, a 3 cm midline incision exposed the right kidney where the ureter was doubly ligated 3-4 mm below renal pelvis. The abdomen was closed and mice were allowed to recover for 3, 7, 14, or 20 days prior to treatment or euthanasia. All animals received humane care as per University of Illinois guidelines; all procedures were approved by the Animal Care Committee at the University of Illinois.

Mesenchymal Stem Cell Isolation and Expansion

MSC were isolated from tibiae and femurs of 4 week-old mice, after marrow cells were plated at a concentration of $2 \times 10^7$ cells per 9.6 cm$^2$ in a 75-cm2 flask with 20 ml MSC media (40% alpha modified Eagle Medium, 40% F-12 Nutrient mixture, 10% heat-inactivated fetal calf serum, and 1% antibiotic-antimitotic solution)[23]. Non-adherent cells were discarded at 72 hours, and adherent cells underwent negative selection using Miltenyi immunomagnetic beads coated with biotinylated antibodies to CD11 b and CD45 (eBiosciences, San Diego, Calif., USA). The resultant culture adherent cells were re-plated at $1 \times 10^6$ cells per 175 cm$^2$, culture expanded to the 4$^{th}$ passage with <1% contamination with CD45+ cells. MSC were administered intravenously via 100 μl Dulbecco's buffered saline (DBS).

Low Level Light Laser and MSC Treatments

Twenty days after UUO (D20 UUO), mice were randomly assigned to 8 treatment groups (n=3 per group); vehicle control (DBS), autologous mesenchymal stem cells (MSC) alone, 635-nm, 532-nm, or 405-nm laser with or without MSC. Low level light laser treatment was administered via research grade 17.5 mW diode laser emitting either 635-nm, 532-nm, or 405-nm, energy density 2.9 J/cm$^2$ via constant wavelength (Erchonia, McKinney, Tex.). A 3 cm diameter area overlying the right kidney was irradiated with the desired wavelength for 300 seconds anteriorly and posteriorly with the animal positioned 8 cm from a rotating laser source. MSC, $1 \times 10^6$ MSCs, were administered intravenously immediately following the laser treatment. Animals underwent euthanasia twenty-four hours following MSC administration.

Histology and Immunofluorescence

Following euthanasia, the right kidneys were excised, divided, fixed in 4% paraformaldehyde in 0.1M phosphate buffer, pH 7.4, paraffin embedded, and sections cut 3 μm thick. Parenchymal changes were examined by sections stained with hematoxylin and eosin (BBC Histo Perfect H&E Staining System, BBC Biochemicals, Mount Vernon, Wash., USA). Masson's Trichrome stain (NovaUltra Special Stain Kit, IHC World, Woodstock, Md.) was used to identify parenchymal fibrosis.

Mitochondrial Activity:

MitoTracker Red CMXRos, M7512 (1 mM solution, intravenously, Molecular Probes, Eugene, Oreg., USA) was administered 30 minutes prior to euthanasia to be concentrated by active mitochondria and retained during cell fixation[24]. Following euthanasia, kidney tissues were immediately frozen in Tissue-Tek and 4-micron thick sections were mounted on glass slides, fixed in ice-cold methanol for 15 minutes at −20 C and counterstained with DAPI solution (300 nM). The slides were imaged on the stage of an inverted microscope (Axiovert 100 M) using the 568-nm laser line for the red label and emission measured via a 585-nm filter[25].

Endothelial Proliferation:

Twenty-four hours prior to euthanasia, BrdU, (10 mg/ml, 300 microliters intramuscularly, Sigma-Aldrich, St. Louis, Mo.) was administered. Tissue sections were stained with primary mouse Biotin anti-BRDU antibody (BrdU In-Situ Detection Kit, BD Pharmingen, San Jose, Calif., USA) and positively stained cells were expressed as an average count per high powered field of 20 high powered fields surveyed (20×) per section. To differentiate between cortical or medullary regions, each slide underwent region delineation by hand and subsequent automated cell counts (Vectra). Proliferating endothelial cells were enumerated as the mean number of cells positively stained for both CD31 (Novus, Littleton Colo.) and BrdU expressed as a percentage of the total positively stained CD31+ cells per high power field with 20 random high power fields counted per section.

Apoptosis:

TUNEL staining was performed for detection of apoptotic cells according to the manufacturer's instructions (DeadEnd Fluorometric TUNEL System, Promega Corporation, Madison, Wis., USA). Tissues samples from naïve kidneys were used as negative control. TUNEL-positive nuclei were counted in a total of 20 random high power fields. Images were acquired and processed with AxioVision (Carl Zeiss International, Gottingen, Germany). Automated cell counts were performed using Vectra Automated Quantitative Pathology Imaging system with inForm Software (Perkin Elmer). Microscopy was performed with the Axio Observer D-1 Microscope, X-Cite Series 120 Q (Carl Zeiss International, Gottingen, Germany).

Immunoassays for TGF-Beta and IL-10

Weighed, cryopreserved renal tissue homogenates were used for the determination of active murine TGF-β1 and IL-10 via ELISA (BD Bioscience, CA, USA). These experiments were conducted as per manufacturer's introductions. Values were expressed as pg/mg protein.

Statistical Analyses

Statistical analysis was performed using Minitab Statistics (State College Pa.). Data were expressed as mean±SE. Significant difference amongst groups was determined by one-way analysis of variance or a two-tailed t-test where $p \leq 0.05$ was considered statistically significant.

Results

Renal Architecture of the Day 20 UUO Model

Figure 6:
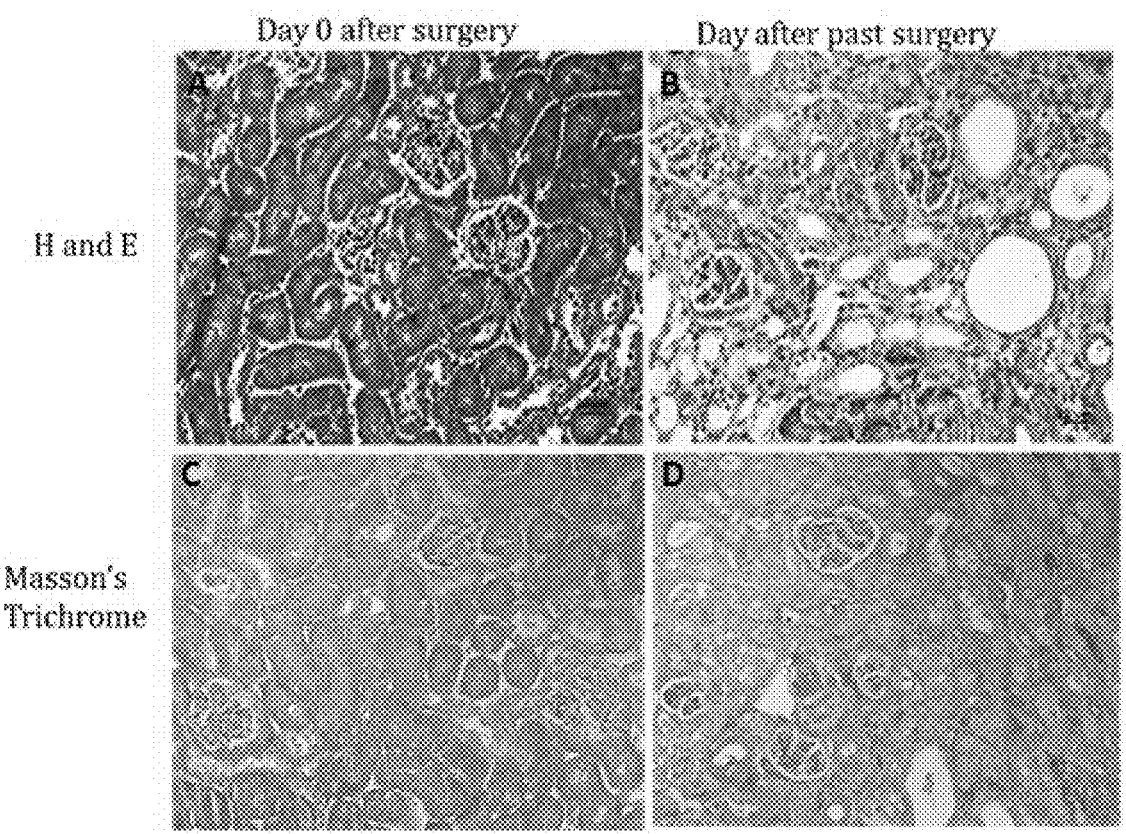
FIG. 6 illustrates histological characteristics of renal fibrosis in UUO (A) nave and (B) fibrotic kidney sample classifying the structural changes as the kidney fibroses (H&E; ×20 magnification). Demonstration of the collagen deposition seen very little in the (C) naïve kidney, but strongly represented in the (D) fibrotic kidney (Masson's Trichrome; ×20 magnification).
Figure 10:
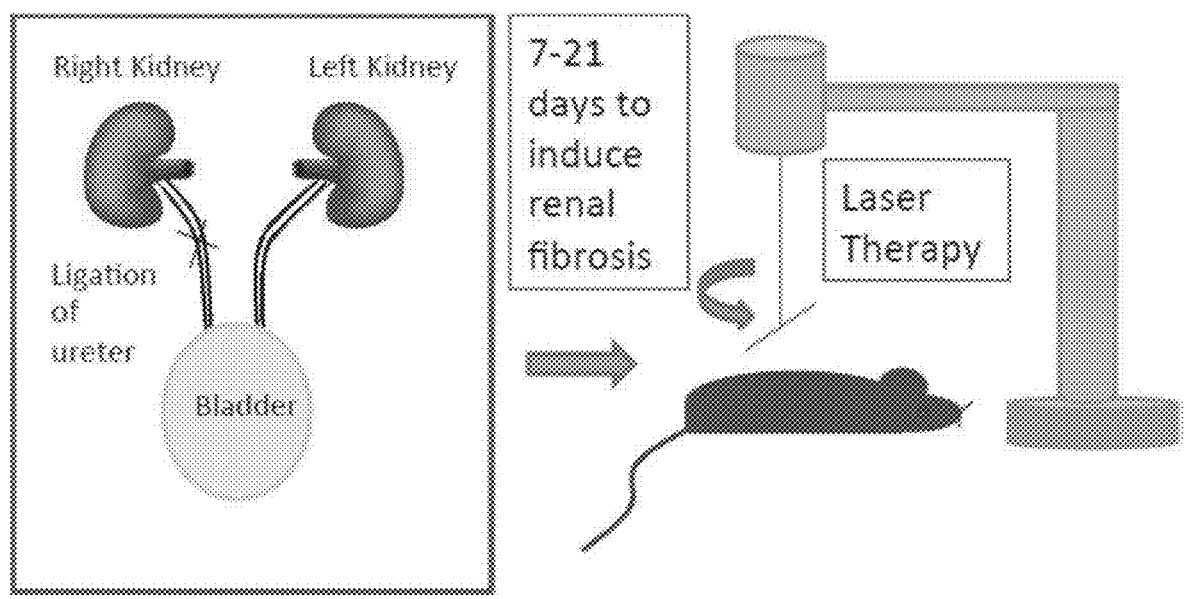
FIG. 10 illustrates the methodology used in the unilateral ureter obstruction model experiments in mice.

Serial culls performed immediately after UUO, and on days 3, 7, 14, and 20 days demonstrated progressive enlargement of renal pelves and calyces with progressive thinning of the remaining cortex (FIG. 10). Appreciable collagen staining was first detected on day 7 with significant increases by day 20 (FIG. 6). Renal tubules demonstrated progressive dilation and finally obliteration and loss. Shrinkage of glomeruli, peritubular capillary endothelial loss and expansion of Bowman's capsule were also observed at day 20. Initial influx of inflammatory mononuclear cells at day 7 diminished over time. These findings indicate the day 20 UUO model demonstrates the pathologic findings of advanced renal parenchymal fibrosis.

MSC Synergize with Low Level Light Laser to Enhance Mitochondrial Activity

D20 UUO mice were treated with a single session of laser to the kidney area. Twenty-four hours later, the mitochondrial membrane potential was measured as a means to define the cell's capacity to generate ATP by oxidative phosphorylation. Alteration of mitochondrial membrane potential (MMP) was detected with Mitotracker Red CMXRos with fluorescent dye administered prior to euthanasia for concentration within the mitochondria, (FIGS. 1 A & B). Applicant observed three significant findings. The 635 nm wavelength significantly increased mitochondrial activity when compared to D20 UUO treatment alone, (2.43±0.45 vs 0.60±0.25, p<0.05). The 532 nm and 405 nm wavelengths and mesenchymal stem cells had modest effects as single modalities (1.32±0.31 (532 nm), 1.50±0.51 (405 nm) and 1.85±0.41 (MSC)). Addition of mesenchymal stem cells to each laser wavelength, significantly exceeded the mitochondrial activity of the D20 UUO group, (5.00±0.67, 6.53±0.91 or 5.11±0.90 vs single modalities 635, 532, and 405 nm, respectively, p<0.05). A pairwise comparison of each MSC based laser treatment to its corresponding laser alone group demonstrated significant increases with the addition of MSC, p<0.05. These findings demonstrate a synergistic effect between each laser wavelength tested and MSC in enhancing mitochondrial activity in fibrotic renal parenchyma.

Reduced Frequency of Apoptosis

Figure 2:
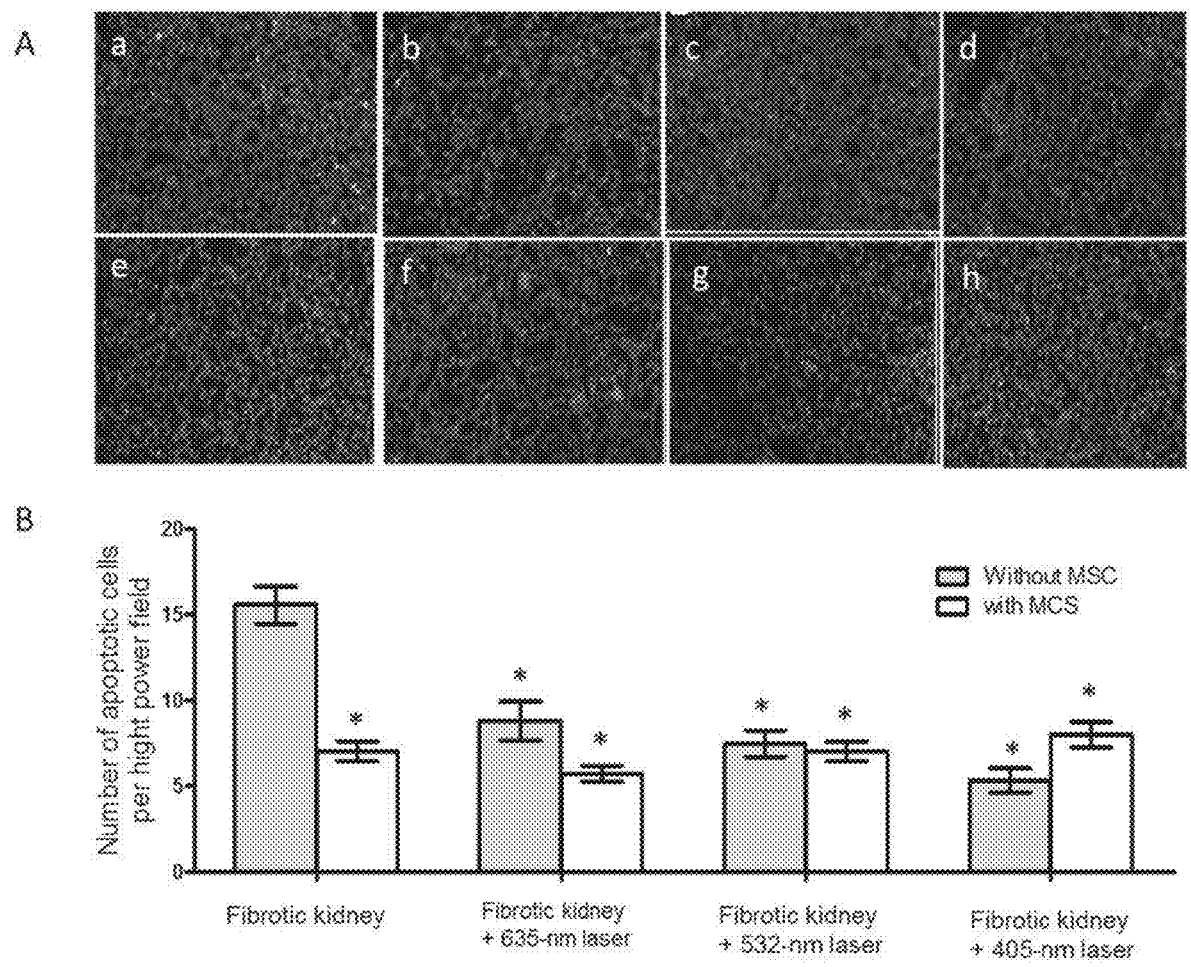
FIG. 2 illustrates apoptotic cells in fibrotic kidney with fluorescent TUNEL staining. A), Images acquired by microscopy with 20× subject lens. (a) Fibrotic kidney, (b) fibrotic kidney+635-nm laser, (c) fibrotic kidney+532-nm laser, and (d) fibrotic kidney+405-nm lase, (e) fibrotic kidney with MSC, (f) fibrotic kidney+635-nm laser with MSC, (g) fibrotic kidney with 532-nm laser with MSC, (h) fibrotic kidney with 405-nm laser with MSC. Spots in the image are the accumulations of fluorescent dye in mitochondria. B), The apoptotic cells were counted by microscopy with 20× objective lane, expressed as mean per high power field (20×). *; p-value<0.05 vs fibrotic kidney without MSC.

Renal fibrosis is associated with ongoing apoptosis and cell loss. Examination of explanted kidneys following fluorescent TUNEL staining was undertaken to determine which treatment groups were effective in reducing apoptosis (FIG. 2). All three wavelengths and mesenchymal stem cells alone significantly reduced the number of apoptotic cells observed when compared to D20 UUO group control. Addition of autologous mesenchymal stem cells to laser treatments did not enhance this effect, suggesting no further gains in apoptosis reduction could be gained by combining treatments (FIGS. 2 A and B).

Figure 3:
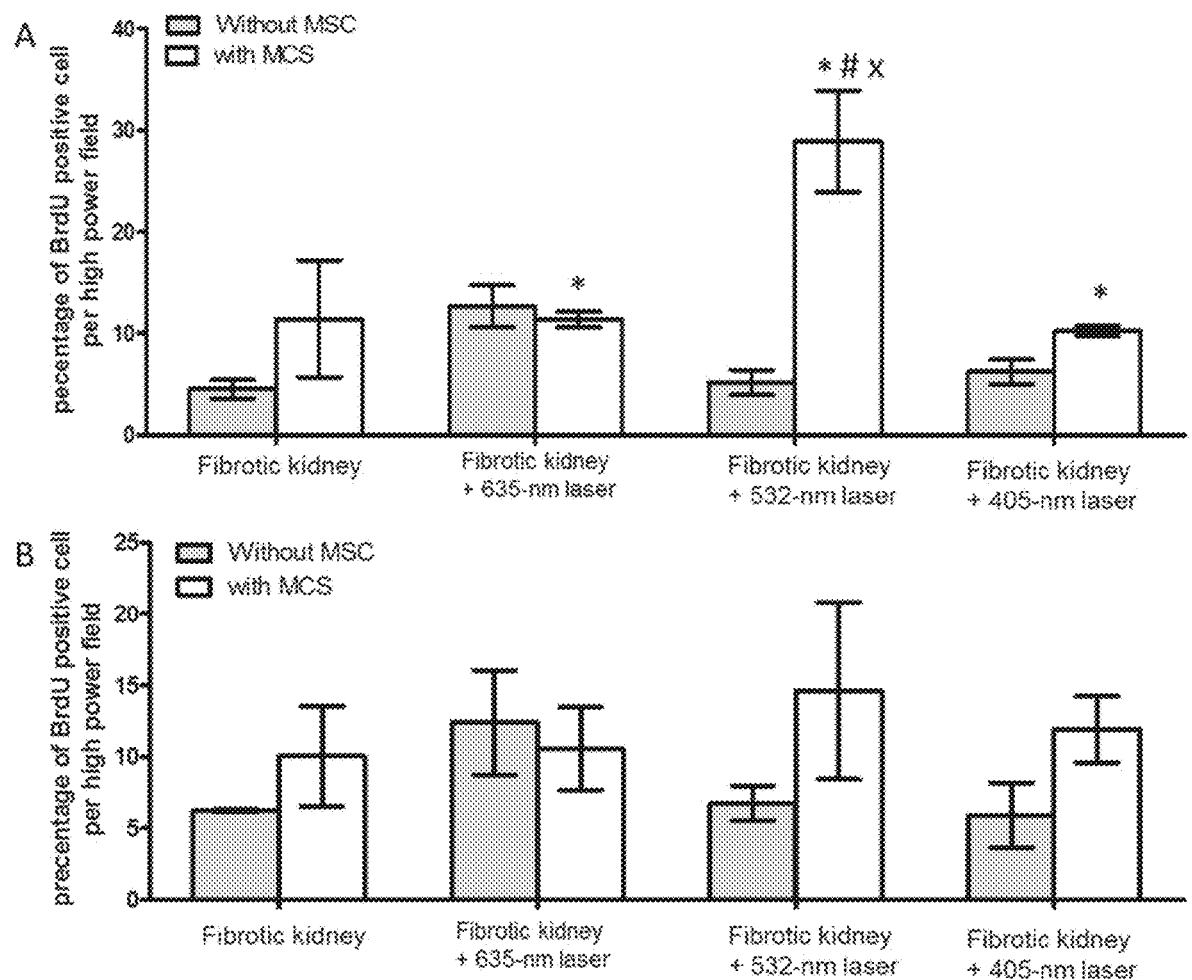
FIG. 3 illustrates proliferation activity of cell in fibrotic kidney. Cell proliferation was detected by BrdU stain. A), BrdU positive cells were counted at cortex area per high power field (20× subjective lens). Percentage of positive BrdU cells per high power field was calculated. *; p-value<0.05 vs fibrotic kidney without MSC, #, p-value<0.05 vs fibrotic kidney with MSC. $^X$; p-value<0.05 vs 532-nm laser treated fibrotic kidney. B), BrdU positive cells were counted at medulla area.
Figure 7:
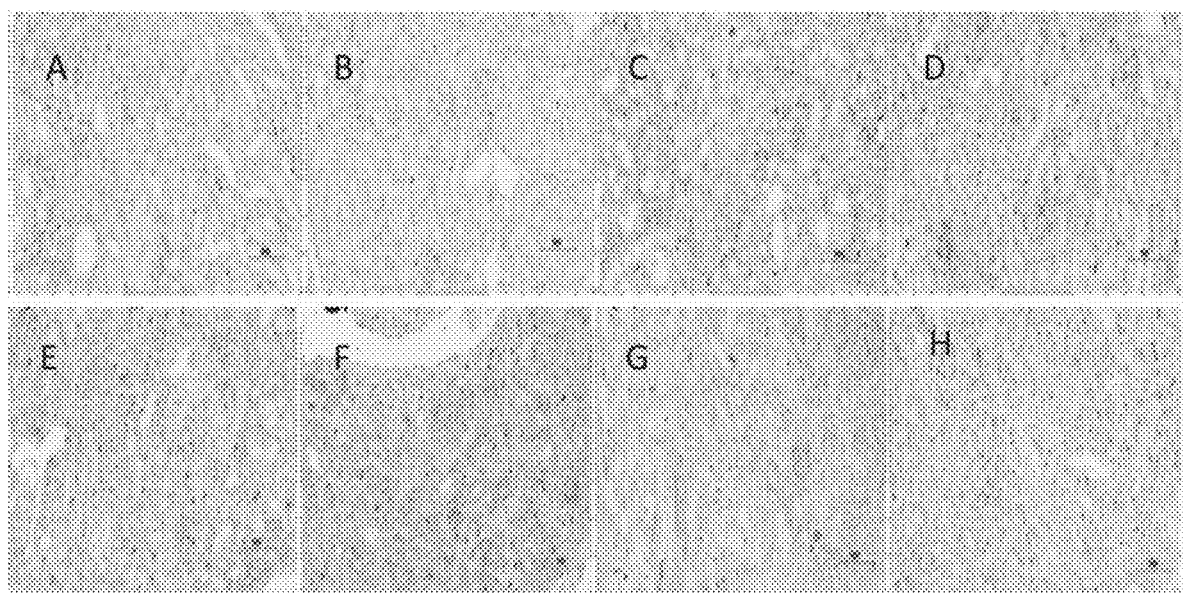
FIG. 7 illustrates proliferation cells in fibrotic kidney. (A) fibrotic kidney, (B) fibrotic kidney+635-nm laser, (C) fibrotic kidney+532-nm laser, and (D) fibrotic kidney+405-nm laser, (E) fibrotic kidney with MSC, (F) fibrotic kidney+635-nm laser with MSC, (G) fibrotic kidney with 532-nm laser with MSC, (H) fibrotic kidney with 405-nm laser with MSC.

MSC Synergize with the 532 nm Wavelength to Enhance Proliferative Activity in the Renal Cortex Cell proliferation detected within fibrotic kidneys can be attributed to the small sub-population of proximal renal tubule epithelial cells which function as progenitor cells, with hematopoietic and mesenchymal stem cells constituting extremely small populations, even after severe organ injury. After division, proximal tubular cells become quiescent for at least 7 days. To examine frequency of proliferating cells specifically in response to the treatment, BRDU was administered immediately following treatments and euthanasia occurred 24 hours later (FIG. 7). Since proximal tubules reside exclusively in the cortex, the frequency of proliferating cells was categorized as either cortical or medullary. Of the two regions, the cortical region appeared to undergo greater proliferative activity than the medulla (FIG. 3). None of the treatment groups demonstrated enhanced proliferation in the medulla. In the cortex, there was a strong trend for all 635 nm lasers to enhance proliferative activity (12.69±2.97 vs 4.50±1.59), however the variability observed between animals precluded statistical significance. Combination of each wavelength laser with MSC demonstrated enhanced proliferation with the 532 nm laser. Analyses revealed combination of 532 nm with MSC was significantly better than UUO alone (28.88±4.97 vs 4.50±1.59 percent, p=0.01), than MSC alone, (28.88±4.97 vs 11.43±1.75 percent, p=0.04) and better than the 532 laser alone, (28.88±4.97 vs 5.15±1.23 percent, p=0.01). The 405 nm and 635 nm wavelengths also synergized with MSC and reached statistical significance.

Figure 4:
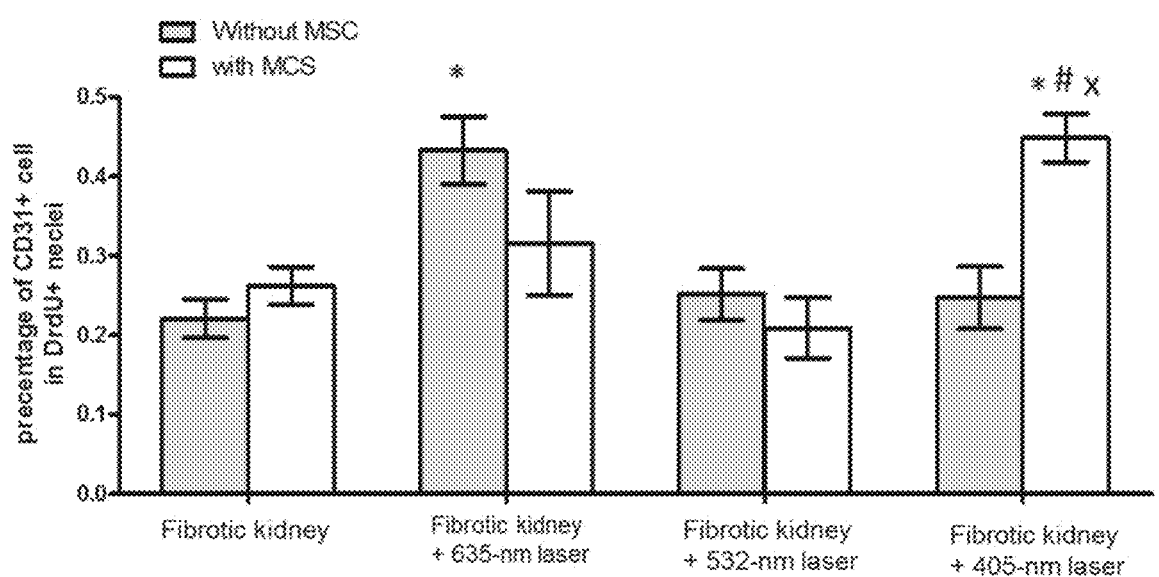
FIG. 4 illustrates endothelial proliferation in fibrotic kidney. Endothelial cells were stained with specific antibody. The cell positive with BrdU and CD31 was counted for proliferation endothelial cells. The data was presented as percentage of CD31+ cells in BrdU positive nuclei. *; p-value<0.05 vs fibrotic kidney without MSC, #, p-value<0.05 vs fibrotic kidney with MSC. $^X$; p-value<0.05 vs corresponding laser treated fibrotic kidney.

MSC Synergize with the 405 nm Wavelength to Enhance Endothelial Proliferative Activity Peritubular capillary loss is associated with tubular atrophy, tubular loss, and interstitial fibrosis. Efforts to enhance endothelial proliferation through VEGF or other means have been shown to mitigate fibrosis. To determine whether laser treatment enhanced endothelial proliferative activity, the frequency of BrdU positive cells also staining positive for the endothelial marker CD31 were compared to the total number of CD31 positive cells (FIG. 4). In all treatment groups the percentage of proliferating cells made up less than 1% of the CD31+ cells. Of the three laser wavelengths, only the 635 nm wavelength appeared to enhance endothelial proliferative activity; no synergy was observed with MSC. Addition of MSC synergized with the 405 nm laser, (0.45±0.04 vs 0.24±0.03, p=0.001 vs 405 nm alone) which slightly exceeded the 635 nm laser alone (0.43±0.07), and significantly exceeded the D20 UUO control, (0.22±0.02, p=0.005), and MSC alone groups (0.26±0.02, p=0.001).

The 532 nm Wavelength Alone or in Combination with MSC Reduces TGF-β

Since the TGF-β pathway plays a critical role in the perpetuation of renal fibrosis, Applicant investigated whether laser treatment would reduce TGF-β production. Only 532-nm laser significantly decreased the TGF-β content, (FIG. 5A); the other two laser wavelengths had no appreciable effect. Addition of MSC alone had no effect, however when combined with the 532 nm laser, there was significantly greater reduction when compared to MSC treatment alone (354.10±33.11 v 1428.00±131.10, p=0.008)

Figure 5:
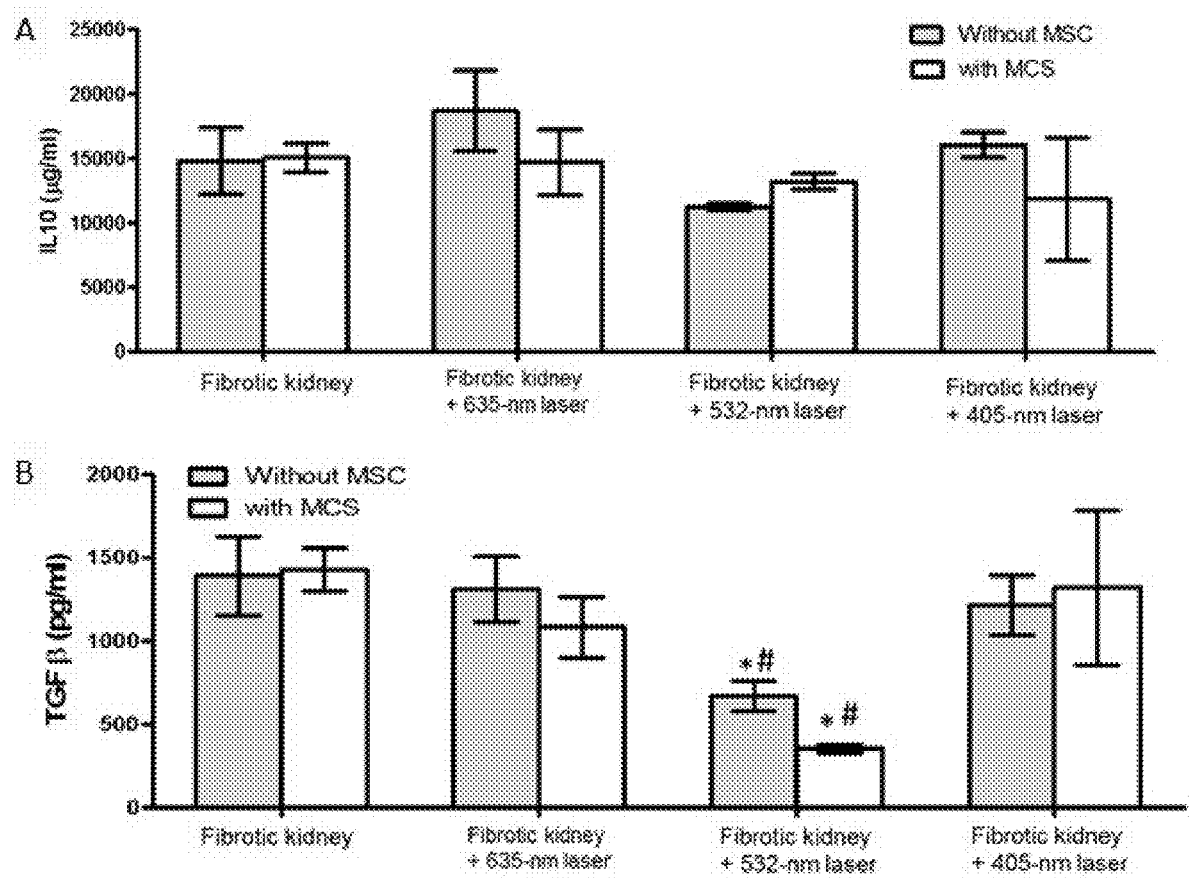
FIG. 5 illustrates the effect of different treatment on the 11_10 and TGF-β amount in fibrotic kidney. A), The alteration of IL-10 in fibrotic kidney with different treatments B), the alteration of TGF-β amount in fibrotic kidney under indicated treatments *; p-value <0.05 vs fibrotic kidney without treatment. #, p-value<0.05 vs fibrotic kidney with NSC treatment.

Since TGF-β can be secreted by tissue macrophages and MSC can convert pro-inflammatory M1 macrophages to IL-10 secreting M2 macrophages, Applicant examined whether laser treatment in combination with MSC could increase IL-10 production (FIG. 5B). Interestingly, the 635-nm treatment alone demonstrated a strong trend for increased IL-10 when compared to D20 UUO (14, 830.00±633.30 vs 18,700±1457.00, p=0.072). None of the other treatment groups showed IL-10 increases.

The Effect of Three, 4-Week, MSC Aided, Tri-Laser Treatment Regimens

Figure 8:
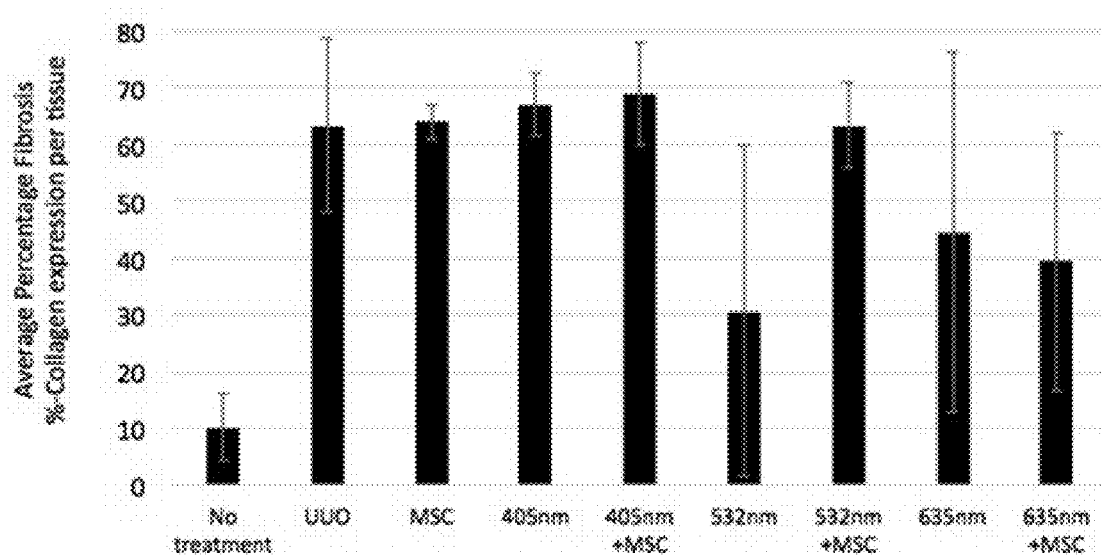
FIG. 8 illustrates paraffin embedded 3 mm thick sections were stained using Masson's trichrome protocol for quantification of fibrosis. Areas of medulla (A) and cortex (B) were hand drawn for each section and the resultant regions were digitally scanned using VECTRA Automated Quantitative Pathology imaging system with inForm software for digital quantification of fibrotic tissue. Percent of tissue staining positively for collagen is expressed on the Y-axis with treatment type on the x-axis.
Figure 8:
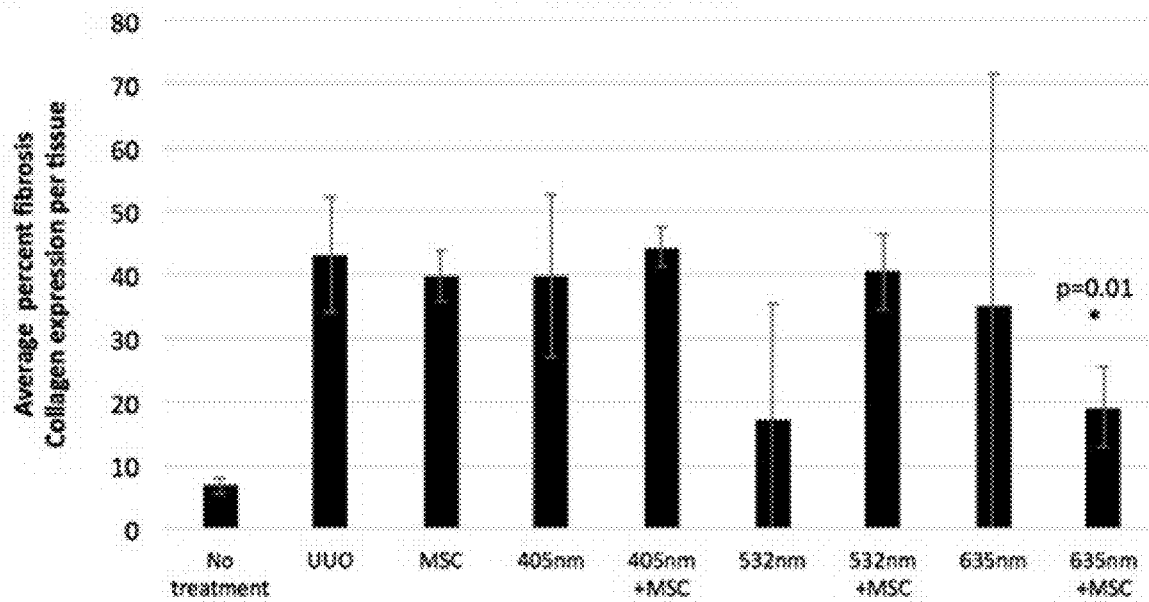
Figure 9A:
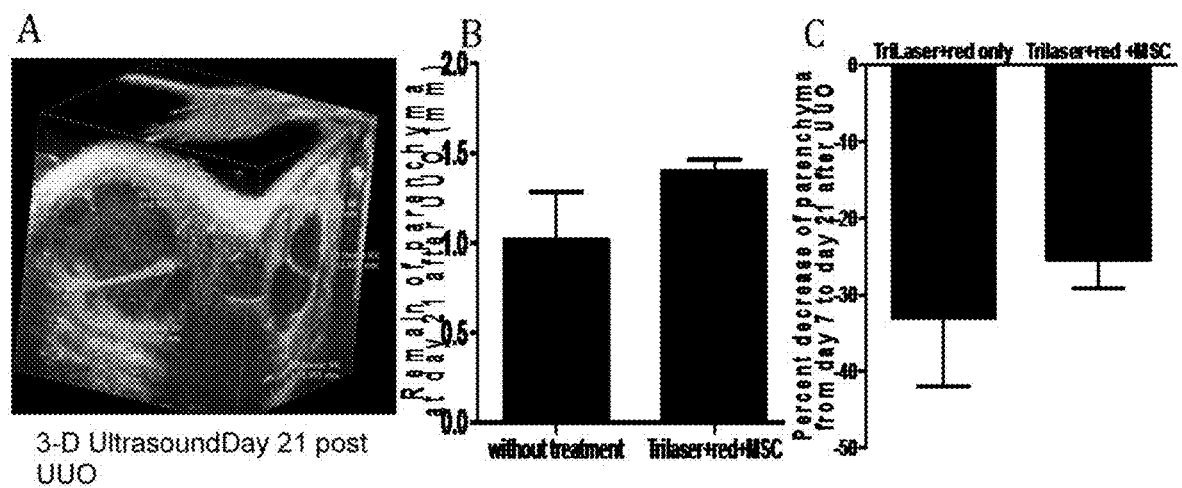
FIG. 9A illustrates 3-D Ultrasound scanning of the UUO treated kidney performed weekly to measure changes in kidney parenchyma (mm), defined as the rim of tissue bordering the hydronephrotic, fluid filled central areas (A). Mean gains in parenchymal dimension following treatment, is measured in mm (B), while percentage of parenchymal loss from the day of UUO is presented in (C), n=3 mice per treatment type for this experiment.
Figure 9B:
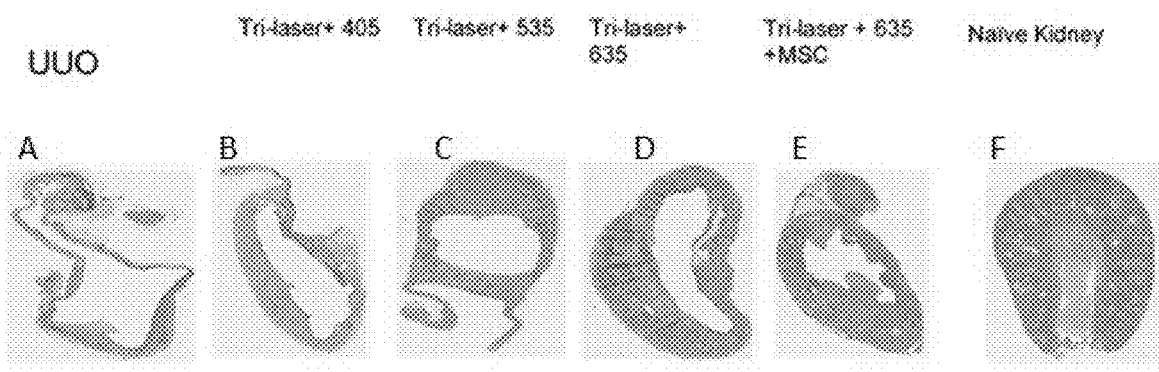
FIG. 9B illustrates mice euthanized at the end of 4 weeks of treatment on day 50, Right UUO treated kidneys were collected, weighed and preserved in neutralized 10% formalin, paraffin embedded, sectioned to 3 mm thick, and stained with Masson's Trichrome procedure. Cross sections of the kidney taken from the upper pole, top third of the kidney were compared to naive, untreated kidneys (A) and UUO treated kidneys (F) for each treatment studied, with representative images shown from each treatment group. UUO treated kidneys demonstrated significant parenchymal loss, with cavitary transformation of the renal pelvis. While tri-laser therapy supplemented with an extra session of 405 nm (B) or 535 nm (C), or 635 (D) nm demonstrated improvement in parenchymal mass, greatest gains and corresponding diminution of the cavitary pelvis, appeared when tri-laser therapy was combined with supplementary laser and mesenchymal stem cells (E).

Animals underwent UUO and all three laser treatment three times weekly in the morning with a single wavelength extra session three times weekly in the afternoon, MSC were administered once a week×14 days. Three-dimensional ultrasound measurements of kidney cortex demonstrates increasing cortical mass after UUO and treatment with tri-laser therapy supplemented with the red 635 laser and MSC. The thickness of the renal cortex was measured on two directions in 3D (see FIGS. 8 and 9).

DISCUSSION

Low level light laser treatments have been used clinically to enhance wound healing, facilitate healing from musculoskeletal injuries, neurologic regenerative strategies, and for the reduction of inflammatory states. Chronic kidney disease shares the need for restoration of epithelium, endothelium, and the reduction of inflammation, and may benefit from low level light laser therapy. In our proof of concept study, Applicant observed that each wavelength, while holding energy density constant, resulted in different effects, providing a unique capacity to either mitigate mechanisms of fibrosis or enhance mechanisms of regeneration.

Progressive apoptosis has been observed in chronic kidney disease. This finding has been linked to mitochondrial deregulation. Pirfenidone, which has a protective effect on mitochondria, can mitigate the development of renal fibrosis, emphasizing the importance of this approach. The 635 nm wavelength was the only single modality treatment group which enhanced mitochondrial activity; addition of MSC to each wavelength led to synergistic effects above that of MSC alone, with the 532 nm and MSC combined treatment group demonstrating greatest gains. When examining reduction of apoptosis, all treatment groups significantly reduced apoptosis. These results suggest that MSC synergize with laser to enhance the amount of ATP available to the cell and reduce apoptosis.

Enhanced proliferation induced by exposure to low level light laser has been well reported. Comparative effects by wavelength was reported by Sroka et al, who tested the proliferative effects of 410, 488, 630, 635, 640, 805, and 1,064 nm laser wavelengths on cultured cells ex vivo. Proliferative effects were observed following a single treatment of either 410 nm, 635 nm, or 805 nm, with a maximum mitotic rate between 4 and 8 J/cm$^2$. At a lower power density, 2.9 J/cm$^2$, Applicant observed proliferative effects in vivo. Detectable endothelial proliferative activity was very low at this stage of fibrosis. Applicant observed enhanced activity in synergy with MSC using the 405 nm wavelength. The 635 nm wavelength alone had similar effects on endothelium. In the renal cortex, all three wavelengths synergized with MSC to enhance proliferation while none or MSC appeared to be effect alone. The 532 nm laser appeared to have the greatest synergistic effect. It is possible that the power density was too low to demonstrate effects by lasers alone on the renal epithelium in the cortex. Defining this consideration would require dose response studies; since the focus of this work was to compare wavelengths holding energy density constant, a dose response study would present the logical next step of investigation. The cortical region which exclusively contains the proximal tubule progenitor cells, demonstrated the greatest proliferative activity. While Applicant cannot definitively conclude our effects specifically targeted this sub-population without fate mapping studies, the results are encouraging and support more in depth examination.

Endothelial proliferation and TGF beta has been examined in cultured endothelial cells ex vivo. Two wavelengths, 635 nm and 830 nm were examined at 2, 4 and 8 J/cm$^2$. Reduction in TGF-beta levels was observed in response to the 830 nm exposure. Differences between these studies may reside not only in radiation energy density used but also light scatter effects when using intact living organisms. The 532 nm wavelength has been used for treatment on hypertrophic scar with substantively higher energy densities, 9.5 j/cm$^2$, 17-22 j/cm$^2$ with a 500 micron spot, or 65-90 j/cm$^2$ with a 200 micron spot. In a review of clinical studies using lasers for the treatment of scars, the pulsed laser wavelength of 585 nm demonstrated some, but low, efficacy. In a model of vocal fold injury induced by the 532 nm wavelength KTP laser administered at 10 W (20 mS pulse width), the absence of fibrotic response was linked to an inflammatory infiltrate and a transient increased expression of MMP-3 and COX-2. Changes in metalloproteinase were also observed with the same wavelength but lower power densities when applied to retinal epithelial cells ex vivo. With a substantive range of power densities, from <1 to 90 J/cm$^2$ for the 532 nm effect on scar and TGF beta and proliferative effects likely to reside below 20 J/cm$^2$, additional study will be required to define whether the 532 nm wavelength should be used at two different energy densities for different desired outcomes or if it can be optimized for both effects using a single energy density.

Combined therapy was tested as an initial tri-laser therapy and MSC plus supplemental single laser therapy to determine the relative contributions of supplemental laser therapy on the reversal of fibrosis. With this initial regimen, tri-laser therapy+MSC+supplement 635 nm therapy appeared to have the greatest reduction on tissue fibrosis (FIG. 9) with 532 nm laser alone appearing to have a trend for a similar effect.

These studies demonstrate tissue specific effects of the lasers which can be augmented or diminished based on a personalized assessment of the pace of tissue regeneration. Both the 635 nm laser and the 532 nm laser were observed to promote potential pro-regenerative activity in the fibrotic kidney after a single dose of laser treatment with the 405 nm laser demonstrating pro-angiogenic effects. Since clinical practices use repetitive treatments to continue the effect of the laser over time and ultimately produce the best patient response, and because Applicant observed each laser to provide a unique beneficial feature on proliferation, apoptosis, pro-angiogenic activity, MSC trafficking and anti-fibrotic activity, all three were combined over 4 weeks for optimal effects with separate treatment groups receiving additional supplemental single laser therapy to focus on the specific benefit of that specific laser.

Applicant has observed that the precise regimen for reversal of fibrosis will depend on the response of the therapy by the tissues being targeted. For example, in two of three animals treated with tri-laser therapy and MSC, there was a tremendous reduction of cortical collagen from fibrotic control (35-52%), with both demonstrating dramatic reversal of collagen deposition to less than 18%. One animal however had a poor response demonstrating significant collagen deposition. Similarly comparison of the medulla showed range of fibrosis in controls to span 68-75% with responders treated with tri-laser therapy, MSC and red laser to drop to <30%. Again, one non-responder was observed. In the case of the non-responder, this animal is likely to have benefited from both 532 and 635 supplemental lasers to augment effect due to the recalcitrant response to fibrosis.

These findings provide the basis for targeted additional study in customizing a laser therapy program of combined wavelengths to optimize MSC effects in reducing and reversing renal fibrosis.

While the disclosure is susceptible to various modifications and alternative forms, specific exemplary embodiments of the present invention have been shown by way of example in the drawings and have been described in detail. It should be understood, however, that there is no intent to limit the disclosure to the particular embodiments disclosed, but on the contrary, the intention is to cover all modifications, equivalents, and alternatives falling within the scope of the disclosure as defined by the appended claims.

The invention claimed is:

1. A method of treating conditions related to diseased or atrophic states of fibrotic tissue, and promoting endothelial preservation and proliferation for muscle or internal organ tissue regeneration and repair in a subject comprising exposing the fibrotic tissue of the muscle or internal organ of the subject to laser light having a wavelength of 405 nm or 532 nm.

2. The method of claim 1 wherein said exposure comprises sequential or simultaneous irradiation of different portions of the fibrotic tissue.

3. The method of claim 1 wherein said exposure comprises at least one scan of the fibrotic tissue with the laser light.

4. The method of claim 1 further comprising administering mesenchymal stem cells to the subject subsequent to exposing the fibrotic tissue to the laser light.

5. The method of claim 4 wherein the mesenchymal stem cells are interferon gamma activated mesenchymal stem cells.

6. The method of claim 4 further comprising exposing the fibrotic tissue to a second exposure of laser light having a wavelength selected from a group consisting of 405 nm, 532 nm, and 635 nm, subsequent to the administering step of the mesenchymal stem cells.

7. The method of claim 1 wherein said exposure reduces or slows cells death in the fibrotic tissue.

8. The method of claim 7 wherein the cell death is through apoptosis.

9. The method of claim 1 wherein the wavelength is selected from the group consisting of 405 nm and 532 nm.

10. A method of treating kidney disease in a subject comprising exposing a kidney and associated nerves to a combination of laser light consisting of wavelengths of 405 nm, 532 nm, and 635 nm.

11. The method of claim 10 wherein said exposure comprises sequential or simultaneous irradiation of different portions of the kidney.

12. The method of claim 10 further comprising administering mesenchymal stem cells to said subject subsequent to exposing the kidney to the laser light.

13. The method of claim 12 wherein the mesenchymal stem cells are interferon gamma activated mesenchymal stem cells.

14. The method of claim 13 wherein the interferon gamma activated mesenchymal stem cells are MHC Class II+ cells.

15. The method of claim 12 further comprising exposing the kidney to a second exposure of laser light having a wavelength selected from a group consisting of 405 nm, 532 nm, and 635 nm subsequent to the administering step of the mesenchymal stem cells.

16. The method of claim 12 further comprising exposing the kidney to laser light having a wavelength of 635 nm.

17. The method of claim 10 comprising first exposing the kidney two or more times to the combination of laser light, administering mesenchymal stem cells subsequent to the first exposing step, and a second exposure of the kidney to laser light having a wavelength selected from a group consisting of 405 nm, 532 nm, and 635 nm subsequent to the administering step of the mesenchymal stem cells.

18. A method of promoting tissue regeneration in a subject comprising exposing the tissue of a muscle or internal organ to a combination of laser light consisting of wavelengths of 405 nm, 532 nm, and 635 nm.

19. The method of claim 18 wherein the internal organ is a kidney or heart.

20. The method of claim 18 further comprising administering mesenchymal stem cells to the subject subsequent to exposing the tissue to the laser light.

21. The method of claim 20 further comprising exposing the tissue to a second exposure of laser light having a wavelength selected from a group consisting of 405 nm, 532 nm, and 635 nm subsequent to the administering step of the mesenchymal stem cells.

* * * * *